United States Patent [19]
Faircloth, Jr. et al.

[11] Patent Number: 5,556,777
[45] Date of Patent: Sep. 17, 1996

[54] IMMUNOSUPPRESSIVE PHARMACEUTICAL COMPOSITIONS NEW BIOLOGICAL ACTIVITY FROM A MARINE AGROBACTERIUM SP.

[75] Inventors: Glynn T. Faircloth, Jr., Cambridge, Mass.; Francisco R. Millan; Librada M. C. Fernandez, both of Leon, Spain; Cristina A. Sarabia, Madrid, Spain

[73] Assignee: PharmaMar, s.a., Madrid, Spain

[21] Appl. No.: 118,989

[22] Filed: Sep. 9, 1993

[51] Int. Cl.$^6$ ............................................. C12N 1/20
[52] U.S. Cl. ........................ 435/118; 435/252.1; 435/170
[58] Field of Search ............................ 435/252.1, 118, 435/170

[56] References Cited

U.S. PATENT DOCUMENTS

| | | | |
|---|---|---|---|
| 4,321,326 | 3/1982 | Stykes | 435/121 |
| 4,532,327 | 7/1985 | Powell et al. | 546/214 |

OTHER PUBLICATIONS

Laskin et al., CRC Handbook of Microbiology, 1985 p. 562.
Berdy et al., CRC Handbook of Antibiotic Compounds 1983 pp. 129, 132, 325, 327.
Bergey's Manual of Systematic Bacteriology, Krieg et al, ed., 1986, p. 251.
Hamana et al, *Can. J. Microbiol.* 36:567–572, 1990.
Cohen, D. J., et al., Ann. Int. Med., 101: 667 (1984).
Tanaka et al., Transplant. Proc., 19(5) Suppl. 6: 11 (1987).
King and Spote, Marine Ecology, 3: 34 (1976).
Kino, T, et al., J. Antibiotics, 40: 1249 (1987).
Kovacs N., Nature, 178: 703 (1956).
Lee J. V., J. Appl. Bacteriol., 50: 73–94 (1981).
Ochiai, T. et al., Transplant. Proc., 19: 1284 (1987).
Powell, R. G. et al., J. Natl. Prod., 44(1): 86–90 (1981).
Powell, R. G. et al., J. Am. Chem. Soc., 105(11): 3739–3741 (1983).
Thornley N. J., J. Appl. Bacteriol., 23: 37–52 (1960).
Van der Auwera, P. et al., J. Microbiol. Methods, 4: 265–275 (1986).
Xu, Q. et al., J. Biol. Chem., 267: 11968 (1992).

*Primary Examiner*—Irene Marx
*Attorney, Agent, or Firm*—Ernest V. Linek

[57] ABSTRACT

The active component of the pharmaceutical composition of the present invention is a compound which has been isolated from the controlled aerobic fermentation of a marine microorganism, Agrobacterium sp. PH-103. The pharmaceutical compositions of the present invention, useful for post surgical graft tolerance, are thus directed to compositions comprising a pharmaceutically acceptable carrier, diluent or excipient, and an effective amount of the compound having the formula:

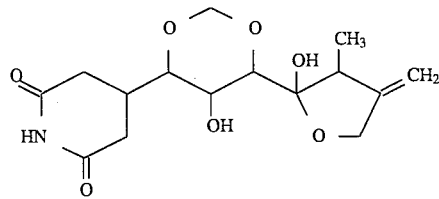

This compound, known as Sesbanimide, is an alkaloid that has been previously been isolated from seeds and reported to be useful as an antitumor drug. Prior to the present invention however, this compound had not been isolated from any fermentation broth nor had it been determined to have immunomodulatory activity.

2 Claims, 4 Drawing Sheets

IMMUNOSUPPRESSIVE PHARMACEUTICAL COMPOSITIONS NEW BIOLOGICAL ACTIVITY FROM A MARINE AGROBACTERIUM SP.

FIELD OF THE INVENTION

Sesbanimide has been newly isolated from the fermentation broth of a marine bacterium Agrobacterium sp. The compound and the fermentation broth demonstrate heretofore unknown immunosuppressive activity.

BACKGROUND OF THE INVENTION

The present invention is directed to novel pharmaceutical compositions which possess immunosuppressive activity, particularly activity which modulates cell-mediated immune responses.

Suppression of the immune response is often required to prevent graft rejection (i.e., graft tolerance) following transplantation surgery. Immunosuppression is also used to inhibit an inappropriate immune response such as autoimmune diseases that often cause severe and debilitating tissue damage. In clinical use today there are natural products for use as immunosuppressants such as fungal metabolites (e.g., Cyclosporin A, FK 506) to prevent graft rejection after transplantation surgery and steroids (e.g., glucocorticosteroids and corticosteroids) to counter inflammation in some autoimmune diseases. However, the therapeutic value of drug discovery in this area would be most immediately realized in the area of organ transplantation. Since 1990 it is estimated that there are approximately 16,000 organ transplantation each year in the United States (Publication, United Network for Transplanted Organs, August 1993). The success of graft tolerance by immunosuppressant drug therapy is well established, but it will continue to require more potent, and less toxic, drugs to reduce morbidities and mortalities associated with them.

Graft tolerance following organ transplantation does not occur unless it is autologous (self) or syngeneic (i.e., between genetically identical individuals; twins); therefore, it must be induced. The immune system which normally acts to reject allogeneic grafts can be inhibited by the use of immunosuppressive drugs. Evidence has accumulated over the years to indicate that the T cell, a functionally and morphologically distinct lymphocyte, is primarily responsible for the rejection of solid grafts by a mechanism referred to as 'cell-mediated'. Cell-mediated immune reactions are cell (lymphocyte)-to-cell (grafted tissue) targeted destruction in lieu of an antibody-to-cell defense. More specifically, there are subsets of T cells that most certainly act to destroy foreign tissue types. Whether cells such as cytotoxic T cells, delayed-type hypersensitivity T cells, or macrophages act alone or in combination, together with T helper cells, to elicit graft rejection remains to be more clearly delineated.

Cyclosporin A, the most prescribed post-transplantation therapeutic agent, is a T cell specific immunosuppressive compound (Cohen et al., *Ann. Int. Med.*, 101:667 (1984)). It works to allow allogeneic graft tolerance by inhibiting normal lymphocyte function, especially T-helper cells (Th). Current data suggests that it blocks IL-2 production and secretion by these cells and, to a lesser degree, IL-1 production by macrophages, possibly inhibiting IL-2 binding to its receptor, and/or inhibiting the chemotactic activity of cyclophilins to recruit eosinophils and neutrophils (Xu et al., *J. Biol. Chem.*, 267:11968 (1992)). Cyclosporin A, although effective, demonstrates considerable toxicity to the recipients of the drug. In particular, there is marked hepatotoxicity associated with its use. Regardless, the specificity of its action is in contrast to the actions of azathioprine metabolites and corticosteroids, which prevent graft rejection by nonspecific effects on lymphocyte function as well as generalized cytotoxicity to bone marrow cells.

FK 506, a second generation immunosuppressive drug, isolated from the fermentation broth of *Streptomyces tsukubaensis* (Kino et al., *J. Antibiotics*, 40:1249 (1987); Kino et al., *J. Antibiotics*, 40:1256 (1987)) has properties similar to Cyclosporin A, but at much greater potencies (Goto et al., *Transplant. Proc.*, 19(5) Supp. 6:11 (1987); Ochiai et al., *Transplant. Proc.*, 19:1284 (1987); Zeevi et al., *Transplant. Proc.*, 22(1): 106 (1990)). Its stronger in vitro and ex vivo characteristics have been demonstrated using primary mixed lymphocyte cultures (MLRs) and secondary proliferation of alloreactive T cells propagated from organ transplantations, respectively (Zeevi et al., *Transplant. Proc.*, 19(5) Supp. 6:40 (1987)). Although FK 506 is more potent than cyclosporin A, similar toxicity profiles to cyclosporin A have been reported and so the search will have to continue for the introduction of an equally effective, but less toxic, immunosuppressive drug.

INFORMATION DISCLOSURE

The following references may be considered important in connection with the review of this specification:

U.S. PATENT DOCUMENTS

U.S. Pat. No. 4,532,327 Powell et al.

OTHER PUBLICATIONS

American Type Culture Catalog 17th edition, 1989. Rockville, Md. U.S.A.

Williams et al., Bergey's Manual of Determinative Bacteriology, 9th edition,

Williams and Wilkins, Baltimore. Md. U.S.A.

Cohen, D. J., et al., *Ann. Int. Med.*, 101:667 (1984)

Goto, T. et al., *Transplant. Proc.*, 19(5) Suppl. 6:11 (1987)

King and Spote, *Marine Ecology*, 3:34 (1976)

Kino, T. et al., *J. Antibiotics*, 40:1249 (1987)

Kovacs N., *Nature*, 178:703 (1956)

Lee J. V., *J. Appl. Bacteriol.*, 50:73–94 (1981)

Ochial, T. et al., *Transplant. Proc.*, 19:1284 (1987)

Powell, R. G. et al., *J. Natl. Prod.*, 44(1): 86–90 (1981)

Powell, R. G. et al., *J. Am. Chem. Soc.*, 105(11): 3739–3741 (1983)

Publication, United Network for Transplanted Organs, August 1993

Thornley N. J., *J. Appl. Bacteriol.*, 23:37–52 (1960)

Van der Auwera, P. et al., *J. Microbiol. Methods*, 4:265–275 (1986)

Xu, Q. et al., *J. Biol. Chem.*, 267:11968 (1992)

Zeevi, A. et al., *Transplant. Proc.*, 22(1): 106 (1990)

SUMMARY OF THE INVENTION

The present invention is directed to pharmaceutical compositions comprising a pharmaceutically acceptable carrier, diluent or excipient and an effective amount of sesbanimide, a compound found to have immunosuppressive activity. Sesbanimide has the following structure:

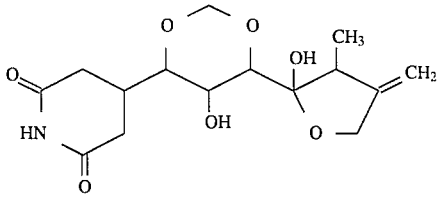

This compound was first isolated from the seed tissue of *Sesbania drummondi* by Powell et al., and found to have antineoplastic activity, particularly against leukemia. See, U.S. Pat. No. 4,532,327, the disclosure of which is hereby incorporated herein by reference.

The present invention is also directed to a fermentation process for producing and accumulating the compound sesbanimide, which comprises cultivating a marine bacterium Agrobacterium species strain PH-103, having Accession No. CECT 4458, under controlled aerobic fermentation conditions in an aqueous nutrient medium at about neutral pH, and at from about 25° to about 30° C., for from about 30 to about 100 hours, whereby isolable quantities of sesbanimide are present in the cultured broth.

The present invention is also directed to the isolated and substantially biologically pure culture of marine bacterium, Agrobacterium species strain PH-103, having Accession No. CECT 4458, useful in the production of sesbanimide.

Finally, the present invention is directed to the cultured broth formed during the controlled aerobic fermentation of the marine bacterium, Agrobacterium species strain PH-103, having Accession No. CECT 4458, in so far as additional active components, in addition to sesbanimide, are believed to exist in said broth. Isolation studies for such undetermined species are currently being conducted.

DETAILED DESCRIPTION OF THE PREFERRED EMBODIMENTS

The Producing Organism

Figure 1:
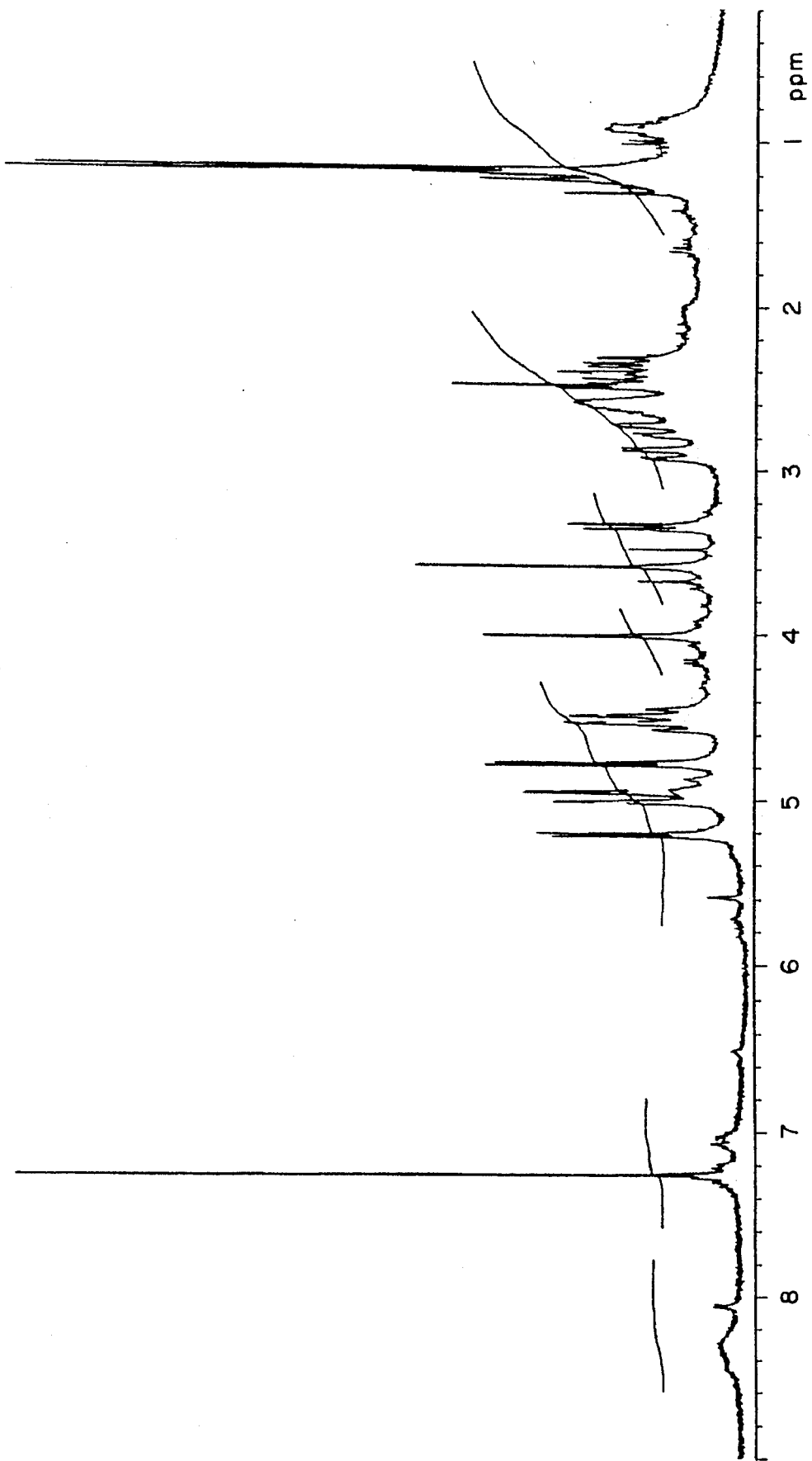
FIG. 1 is an $^1$H NMR spectrum of sesbanimide, produced and isolated according to the present invention.

The microorganism utilized for the production of the immunosuppressive activity found in the broth and of sesbanimide is Agrobacterium species strain PH-103, a culture of which has been deposited in the Colección Española de Cultivos Tipo at the Universidad de Valencia, Spain with the accession number CECT 4458. This deposit was made under the provisions of the Budapest Treaty and all restrictions on the availability thereof to the public will be irrevocably revoked upon the granting of this application.

The organism was isolated from the marine tunicate *Ecteinascidia turbinata* collected in the mangroves of the Florida peninsula (U.S.A.). This organism has the following characteristics which correlate well with previously reported marine Agrobacterium. The taxonomic methods used herein were those reported in Table 1. The media or test and appropriate references for taxonomic studies are as follows:

TABLE 1

1. Colonial morphology—Marine agar medium (Difco)
2. Cell morphology—ATCC medium number 231 in American Type Culture Catalog, 17th edition, 1989
3. Oxidase—Kovacs N., *Nature,* 178:703 (1956)
4. Urease—Urease medium (Difco)
5. Salt tolerance—Growth at NaCl concentration up to 10% in Tryptone 1%
6. Acid from carbohydrates—Semisolid O/F basal medium (Difco) added filter-sterilized aqueous solutions of carbohydrates to a final concentration of 1%
7. Growth on single carbon sources—2.7% Instant Ocean Salts used as basal medium with filter sterilized carbon sources to a final concentration of 1% (v/v)
8. Growth in Triple Sugar Iron (Difco)
9. Amylase—Cowan S. T. Cowan and Steel's Manual for the Identification of Medical Bacteria, 2nd edition, University Press, Cambridge, 1974
10. Arginine dihydrolase. Thornley N. J., *J. Appl. Bacteriol.,* 23:37–52 (1960)
11. Coagulase—0.2% (w/v) final concentration Bovine plasma albumin basal medium
12. Lecithinase—10% (v/v) egg yolk emulsion in ATCC number 231 basal medium
13. Lipase—Lipolytic activity against Tween 20 and Tween 60 1% (v/v) in ATCC number 231 basal medium
14. Indole—Lee J. V., *J. Appl. Bacteriol.,* 50:73–94 (1981)
15. Tyrosinase—0.5% (w/v) tyrosine in ATCC number 231 basal medium
16. Phosphatase—Filter-sterilized 1% solution of the sodium salt of phenolphthalein diphosphate to give a final concentration of 0.01% in ATCC number 231 basal medium.
17. Motility and flagellation—Mayfield C. I. and Inniss W. E., *Can. J. Microbiol.,* 23:1311–1313 (1977)
18. Antibiotic sensitivity—ATCC number 231 basal medium. Difco sensitivity discs
19. Fatty acids analysis—Van der Auwera et al., *J. Microbiol. Methods,* 4:265–275 (1986)

The culture was incubated at 27° C. and records of the results were made after suitable incubation times. All media were prepared with 2.7% Instant Ocean Salts and pH was approximately neutral (7–7.4). The description of the culture and test results are as follows:

Colonial morphology: colonies are low convex, circular, smooth, mucous, non-pigmented to light beige after 2–5 days incubation time.

Cell morphology: Gram negative nonsporing, motile rods, mostly singly in young cultures. In older cultures, strain PH-103 develops rossetta-shaped aggregates. Motile by peritrychous flagella.

Aerobic possessing a respiratory type metabolism with oxygen as the final electron acceptor.

The catalase and oxidase are positives and urease negative.

Salt tolerance: unable to grow below 1% NaCl, the optimum salt concentration for it's growth being between 5–8%.

Biochemical properties: acid is produced from glycerol, no acid is produced from glucose, mannitol, maltose, saccharose, arabinose, sorbitol, or xylose. Growth on phenylalanine, ornithine and lysine; no growth on alanine, proline, histidine, glycine, D-fructose, acetate or methanol. No $SH_2$ produced, no starch-hydrolysis, no gelatin liquified, skim milk not coagulated. Lecithinase, lipase, tyrosinase, phosphatase, arginine dihydrolase not produced. No indole detected.

Antibiotic sensitivity: resistant to vancomycin and polymyxin. Sensitive to nalidixic acid.

The fatty acids profile of strain PH-103 correlates well with that of several other marine Agrobacterium species, including A. aggregatum NCIMB 2208, the most similar one amongst all the marine Agrobacterium studied (A. aggregatum NCIMB 2208, A. agile NCIMB 2207, A. atlanticum DSM 5823, A. ferrugineum NCIMB 1537, A. gelatinovorum NCIMB 2206, A. kielense NCIMB 2205, A. luteum NCIMB 1538, A. meteori DSM 5824, and A. sanguineum NCIMB 1539.

Table 2 shows a comparison of the fatty acids fingerprinting of PH-103 and of the most related marine Agrobacterium. The methyl esters of the fatty acids (FAMEs) were identified by their equivalent of chain length after gas-chromatographic separation in a Ultra 2 capillary column (Hewlett-Packard) using nitrogen as the carrier gas.

are needed, at least when the organism is isolated from a marine source, as those found in sea water such as sodium chloride, sulfate, thiosulfate, carbonate, bicarbonate, bromide, etc., and potassium chloride, magnesium chloride or sulfate, etc.

With the use of tryptone and yeast extract as nitrogen sources, and glucose and maltose as carbon sources, and several of the sea water salts above mentioned, good antitumoral and immunosuppressive activities are obtained. In Table 3, two media compositions providing a compound with good antitumoral and immunosuppressive activities are shown.

The skilled artisan will appreciate the fact that the above mentioned media are merely examples of media suitable for the production of sesbanimide by the presently disclosed strain of Agrobacterium. It is believed that a wide range of nutrient media may be substituted for those dislcosed herein, with good growth and production resulting therefrom. Also, it is well known that once a microorganism has been discovered to produce a substance, many other more or less related microorganisms can be isolated with a similar production properties.

All cultures and fermentations must be conducted in sterile media and conditions. To start a fermentation, it is necessary to seed it with an inoculum grown in a medium similar to those already described for the fermentation. The

TABLE 2

| Microorganism | FAME equivalent chain lengths (%) | | | | | | | | | | |
|---|---|---|---|---|---|---|---|---|---|---|---|
| | 11.81 | 12.00 | 14.53 | 15.81 | 16.00 | 17.82 | 18.00 | 18.08 | 18.82 | 19.84 | 20.00 |
| PH-103 | <1 | <1 | <1 | <1 | <1 | 68.71 | 5.27 | 12.34 | <1 | 11.62 | 1.23 |
| A. aggregatum NCIMB 2208 | <1 | <1 | 1.27 | <1 | <1 | 63.33 | 5.15 | 9.29 | <1 | 14.24 | 1.30 |
| A. kielense NCIMB 2205 | <1 | <1 | <1 | <1 | <1 | 84.05 | 4.11 | 6.11 | 1.03 | 1.36 | <1 |
| A. meteori DSM 5824 | <1 | 3.05 | <1 | <1 | 9.32 | 69.42 | 2.15 | 13.64 | <1 | <1 | <1 |
| A. gelatinovorum NCIMB 2206 | 2.82 | <1 | <1 | 1.50 | 9.92 | 70.62 | <1 | 13.14 | <1 | <1 | <1 |

A careful comparison of the foregoing data with published descriptions including Bergey's Manual of Determinative Bacteriology (9th, edition) of known microorganisms reveals the inclusion of this strain in the genus Agrobacterium. Some properties of the culture were considered to be too different from those of known species of the genus. On this basis it was designated Agrobacterium sp., strain PH-103.

FERMENTATION OF THE PRODUCING ORGANISM

Sesbanimide is newly produced in this invention by the controlled fermentation of a microorganism. This microorganism is preferably grown in an aqueous nutrient medium, under aerobic and mesophilic conditions, preferably between 24° C. and 35° C. at a pH ranging between about 6.0 and 8.0. The length of the fermentation typically ranges between 24 h and 168 h, preferably between 24 h and 96 h. A good production can be obtained at 28° C. and a pH 7.0 to 7.5. The rate of growth of the organism is logarithmic during the first 48 h and the antitumoral, and immunosuppressive activity are maximal at 72 h, stopping when the pH is over 8.0. The nutrient medium employed should preferably be composed of any suitable nitrogen source such as protein hydrolysates, or protein and/or isolated amino acids, or any ammonium and/or nitrate source; as source of carbon any assimilable carbohydrate and/or fat, and a source of salts percentage of inoculum typically needed ranges between 1 and 10%, 5% being typically preferred.

TABLE 3

| | Medium 1 | Medium 2 |
|---|---|---|
| Tryptone | 20 g | — |
| Yeast extract | 5 g | 5 g |
| Casein | — | 20 g |
| Dextrose | 20 g | — |
| Glycerol | — | 20 g |
| MOPS | 2 g | — |
| $CaCO_3$ | — | 4 g |
| Trace elements solution[1] | — | 1 ml |
| Instant Ocean Salts[2] | 27 g | — |
| Distilled water | — | 1000 ml |
| Tap water | 1000 ml | — |

[1]See ATCC medium number 237. American Type Culture Collection Catalog. 1989
[2]See King and Spote, Marine Ecology, 3: 34 (1976) Adjust pH to 7.4 in all the three mentioned media with an alkali solution.

ISOLATION AND PURIFICATION OF SESBANIMIDE FROM BROTH

Isolation and purification of the sesbanimide produced by fermentation is typically conducted using a combination of extraction and chromatographic techniques. A preferred sequence of steps is as follows:

Extract the filtrate broth with an immiscible solvent such as ethyl acetate. Combine these extracts and concentrate to dryness in vacuo. Dilute the residue extract with NaCl 10%/methanol (1:1) and partition it with an immiscible solvent such as hexane which is capable of removing the lipids an another impurities of low polarity. Remove the active materials from the aqueous alcohol fraction by partitioning with an appropriate solvent such as ethyl acetate and dichloromethane. The recovered solvent phases constitute the crude active extract.

Further separation and purification of sesbanimide from the crude extract can be affected by the use of the proper combination of chromatographic techniques, including, for example, column chromatography (CC), preparative medium pressure liquid chromatography (MPLC) and thin layer chromatography (TLC). Fractionation may be guided by antitumoral and immunosuppressive activities.

Figure 2:
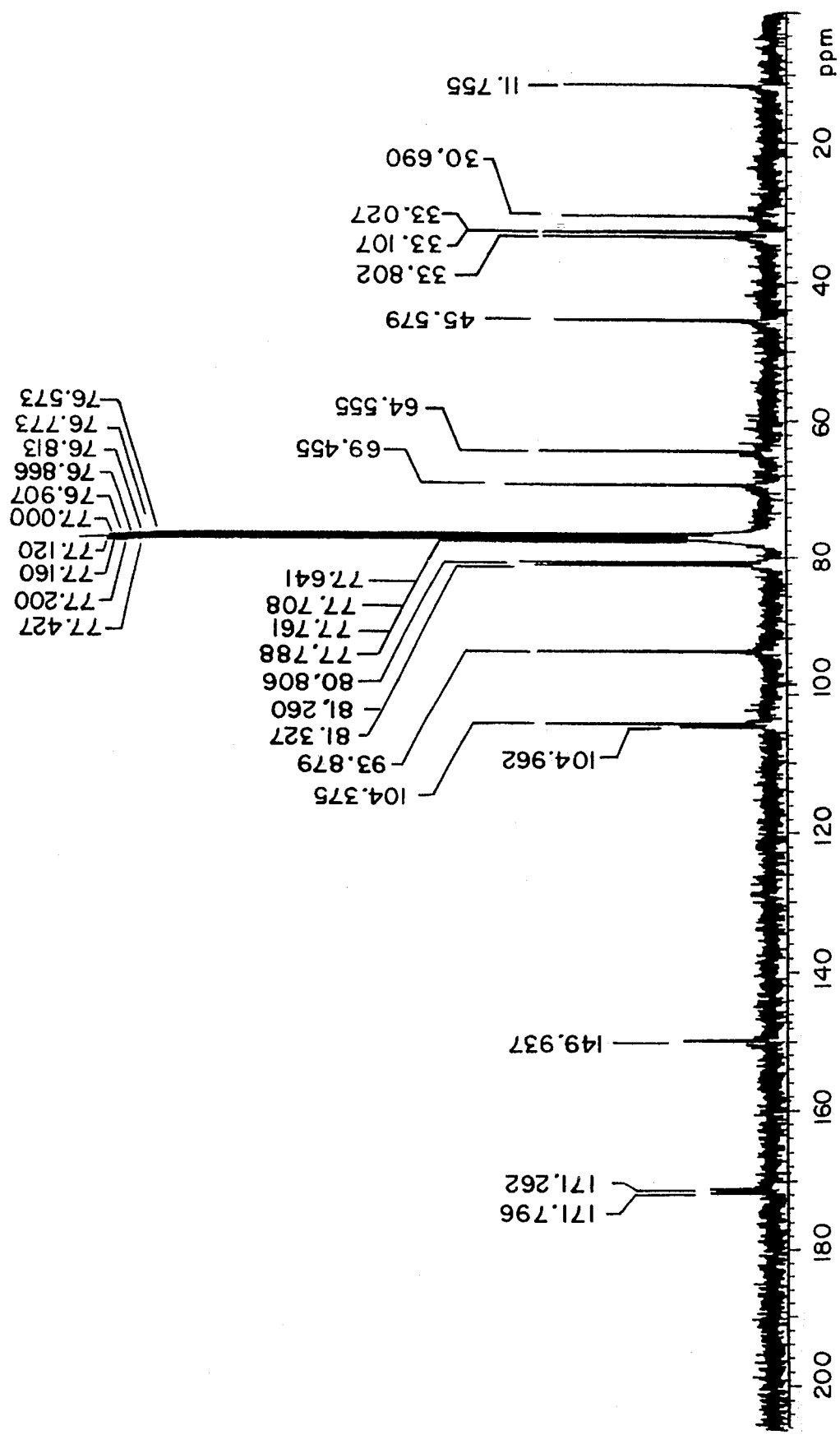
FIG. 2 is a $^{13}$C NMR spectrum of the sesbanimide produced herein.
Figure 3:
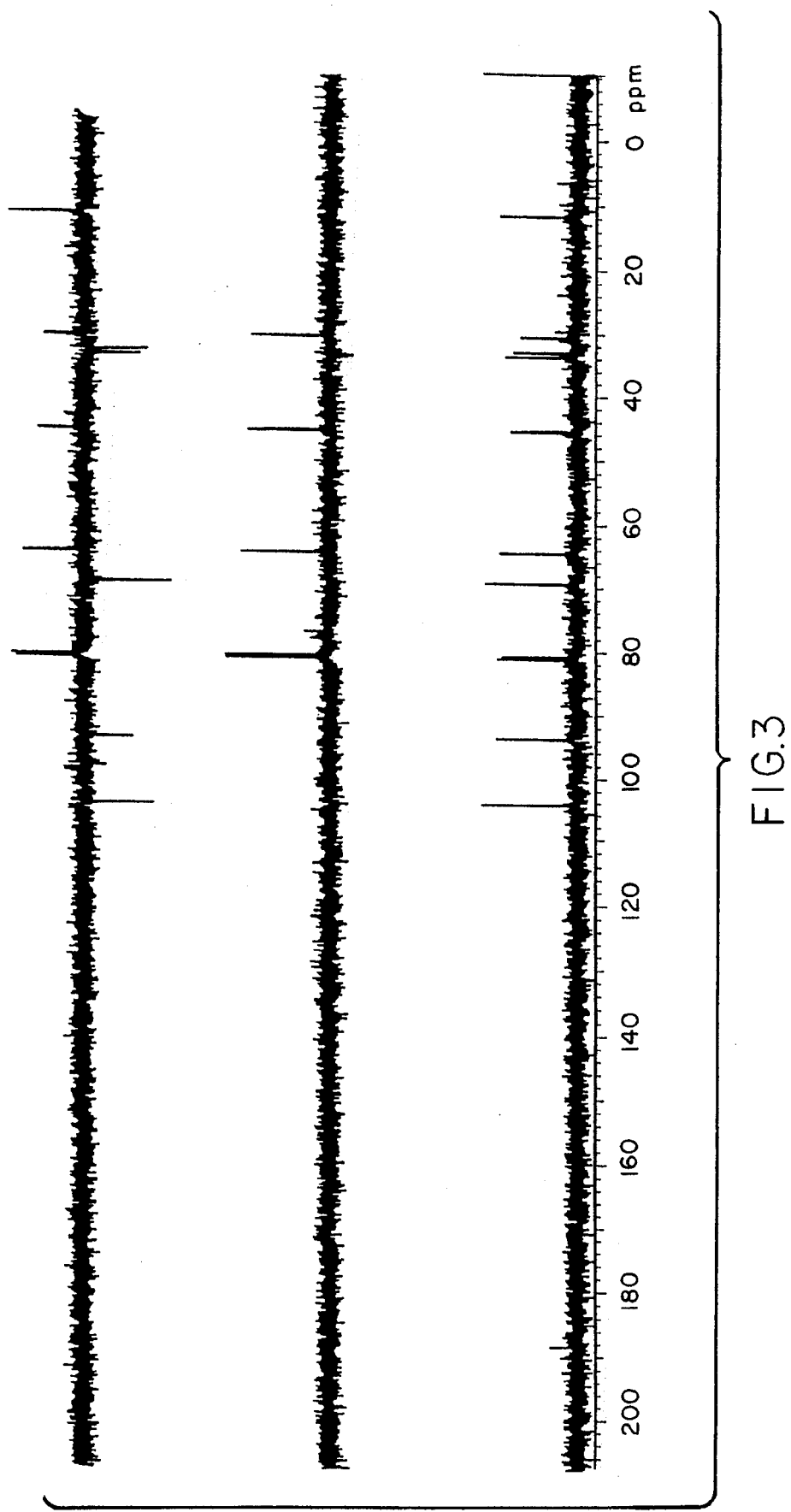
FIG. 3 is a DEPT (Distortionless Enhacement By Polarization Transfer) spectrum of the sesbanimide produced herein.
Figure 4:
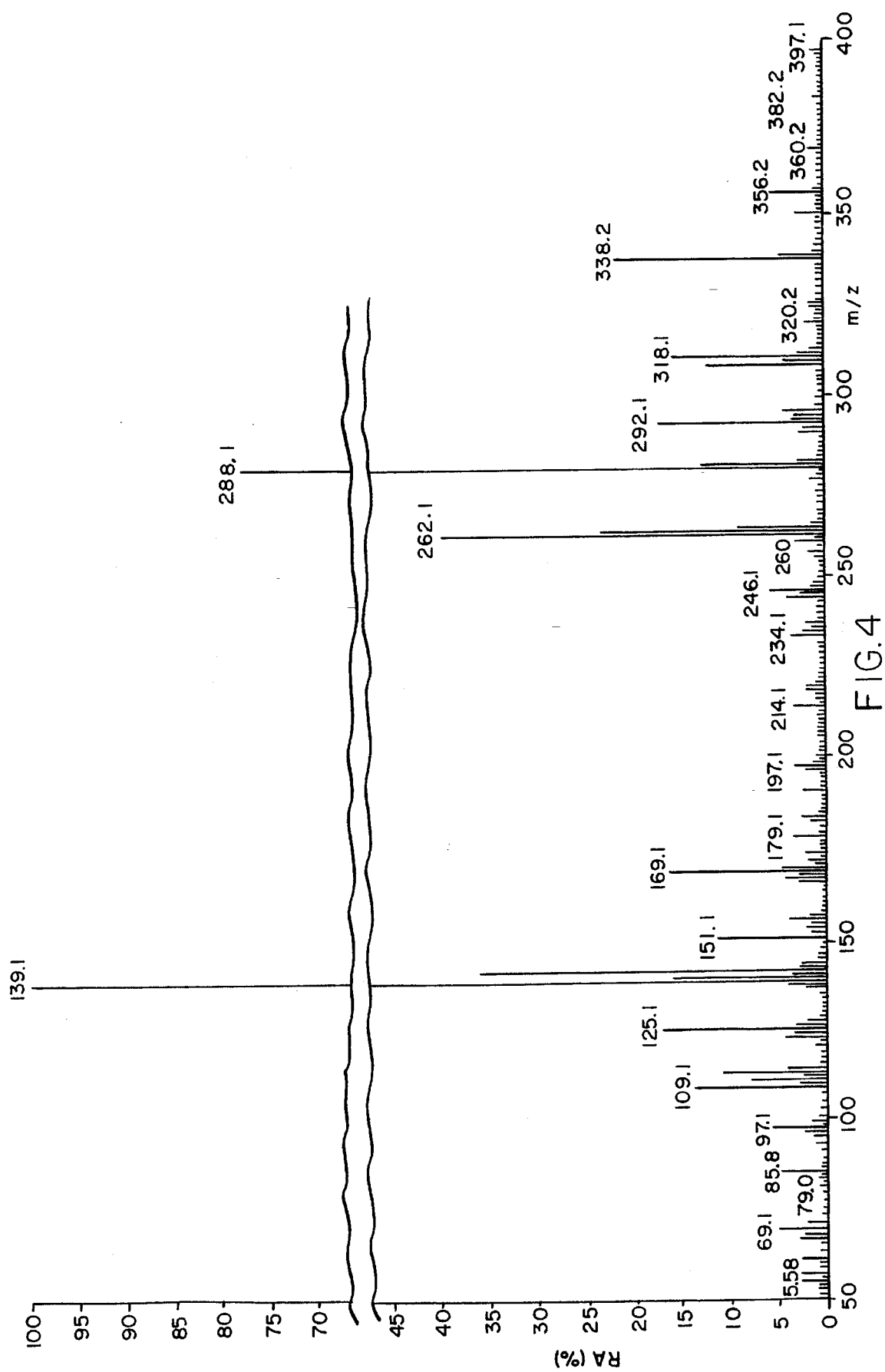
FIG. 4 is a Mass spectrum of the sesbanimide produced herein.

On the basis of detailed analysis of their various spectral characteristics, the pure compound was identified as sesbanimide (see $^1$H NMR, $^{13}$C NMR, DEPT, and Mass spectra reproduced in FIGS. 1, 2, 3, and 4, respectively)

BIOLOGICAL PROPERTIES OF SESBANIMIDE AND PH-103 FERMENTATION BROTH

The immunomodulator compound of the present invention, sesbanimide, is believed to be especially useful as an immunosuppressive drug for the treatment of post surgical graft rejection and related clinical conditions such as autoimmune illness to one's own tissues.

The following Table (4) illustrates the immunosuppressive activity discovered for the compound sesbanimide:

TABLE 4

In Vitro Immunosuppressive Activity and Cytotoxicity of Sesbanimide in a Murine Mixed Lymphocyte Reaction (MLR) and Lymphocyte Viability Assay (LcV).

| Fractions containing Sesbanimide (S) | MLR $IC_{50}$ µg/ml | LcV $IC_{50}$ µg/ml | Index Cytotox./ Activity | Composition |
|---|---|---|---|---|
| PH-103 broth[1]f | <0.375000 | 37.900 | >101 | E |
| ET 103/44-3:4a | <0.015000 | >50.000 | >>3,333 | M |
| ET 103/47-8a | <0.015000 | >50.000 | >>3,333 | M |
| ET 103/64-6:8a | <0.007500 | 13.100 | >1,746 | S |
| ET 103/83-4b | <0.015000 | >50.000 | >3,333 | E |
| ET 103/84-5b | 0.003600 | 3.670 | 1,037 | E |
| ET 103/87-6c | <0.000150 | >0.500 | >>3,333 | CF |
| ET 103/88-1d | <0.000015 | >0.050 | >>3,333 | CF |
| ET 103/89-4e | 0.000150 | 0.417 | 2,777 | S |

[1] ml fermentation broth
(a) Test date: 6-25-92
(b) Test date: 4-29-93
(c) Test date: 5-28-93
(d) Test date: 6-11-93
(e) Test date: 6-18-93
(f) Test date: 7-29-93
S Sesbanimide
M Fraction containing Sesbanimide as a minor component
E Broth Extract containing Sesbanimide
CF Chromatographic fraction containing Sesbanimide The data from Table 4 illustrate the potent immunosuppressive activity of sesbanimide, whether in trace amounts of an extract, as a major constituent of an isolation fraction, or as a pure compound. Moreover, these results indicate that the immunosuppression may be achieved noncytotoxic means. That is, sesbanimide showed more than a 3 log separation of its cytotoxicity ($IC_{50}$ of between 417 ng/ml–3,600 ng/ml) to biological activity ($IC_{50}$ of between 0.150 ng/ml–3.6 ng/ml) using an in vitro cell-mediated immune response.

TABLE 5

Toxicology of Sesbanimide in CD-1 or CB6F1 Mice.

| Fraction containing Sesbanimide | Maximum Tolerated mg/kg | Alive Day 5 % | $LD_{50}$ mg/kg | Composition |
|---|---|---|---|---|
| ET 103/78-13:15[a] | 125 | 100% | 212.5 | M |
| ET 103/81[a] | 300 | 100% | >300 | M |
| Sesbanimide[b] | 0.56 | 100% | 0.805 | S |

[a] Test date: 1-14-93
[b] Test date: 8-05-93

Table 5 shows the in vivo toxicity data for sesbanimide. As a pure compound sesbanimide is toxic at 56, 10.5 and 5.6 mg/kg, but it showed no toxicity at total doses equal to or lower than 0.56 mg/kg. An $LD_{50}$ determination of 0.805 was made between 1.05 and 0.56 mg/kg/total dose from a QD 1–7 experiment in CB6F1 mice.

TABLE 6

In Vivo Immunosuppressive Activity of Sesbanimide in a Graft-v-Host Reaction.

| Fraction containing Sesbanimide | Optimal Dose mg/kg | Alive Day 8 % | Index | Composition |
|---|---|---|---|---|
| ET 103/71[a] | 7.5 | 100% | 1.02 | M |
| ET 103/47[a] | 1.0 | 100% | 0.99 | M |
| Positive[a] | — | 100% | 1.32 | — |
| Syngeneic[a] | — | 100% | 0.99 | — |
| Cyclophosphamide[a] | 200.0 | 100% | 0.23 | — |
| Nonspecific[a] | — | 100% | 0.96 | — |
| Sesbanimide | 0.2 | 40% | 0.92 | S |
| Positive[a] | — | 100% | 1.34 | — |
| Syngeneic[b] | — | 100% | 0.99 | — |
| Cyclophosphamide[b] | 200.0 | 60% | 0.28 | — |
| Nonspecific[b] | — | 100% | 0.91 | — |

[a] Test date: 1-24-93
[b] Test date: 8-11-93

The GVHR is the direct in vivo correlation of the in vitro MLR immune reaction used to determined immunomodulation. Data from Table 6 illustrates the potent immunosuppressive activity of Sesbanimide. It is also clear that immunosuppression has occurred when sesbanimide is either a minor constituent or the pure compound responsible for biological activity.

TABLE 7

In Vivo Immunosuppressive Activity of Sesbanimide after Transplanted Skin Grafts.

| Fraction | Optimal Dose mg/kg | Alive Day 15 | Mean Graft Survival % Days ± SD |
|---|---|---|---|
| ET 103/78-13:15[a] | 10 | 100% | 8.7 ± 1.7 |
| ET 103/81[a] | 25 | 67% | 7.7 ± 4.1 |
| Positive[a] | — | 100% | 4.4 ± 1.0 |
| Cyclosporin A[a] | 200.0 | 100% | 6.7 ± 1.1 |

[a] Test date: 2-1-93

Skin grafting is used to determine the application of a new immunosuppressive compound in transplantation surgery. Table 7 demonstrates the continued immunosuppressive activity from sesbanimide containing fractions in this transplantation model. However, the response is only from a fraction with sesbanimide as a minor component and current studies are ongoing to determine if Sesbanimide alone is more potent than the above indicated response.

The immunosuppressive composition of the present invention may be employed in combination with other therapeutic agents for the treatment of the above defined conditions. Examples of such further therapeutic agents include agents that are presently believed to be effective for potentiating graft tolerance or associated conditions in autoimmunity such as the DNA alkylating agents cyclophosphamide (cyclostin, cycloblastin, endoxan, neosar, procytox and sendoxan) and chlorambucil, which have been used to potentiate immunotolerance, metabolites of azathioprine (imuran, imurel, azoran, azanin, azamune) and 6-mercaptopurine to reduce monocytes and inhibit K cell activity, while cyclosporin A (sandimmune, ciclosporin, cyclosporin A) and FK 506 specifically inhibit T-cell function. The component compounds of such combination therapy may be administered simultaneously, in either separate or combined formulations, or at different times, e.g., sequentially such that a combined effect is achieved.

The immunosuppressive composition according to the present invention may be administered for therapy by any suitable route including oral, rectal, nasal, topical (including buccal and sublingual), vaginal and parenteral (including subcutaneous, intramuscular, intravenous and intradermal). It will be appreciated that the preferred route will vary with the condition and age of the recipient, the nature of the condition and the active ingredients.

In general a suitable dose for each of the above-mentioned conditions (e.g., transplantation or autoimmune therapy) will be in the range of from about 1 to 50 mg per kilogram body weight of the recipient (e.g., a human) per day, preferably in the range of from about 5 to 20 mg per kilogram body weight per day and most preferably in the range of from about 10 to 15 mg per kilogram body weight per day. The desired dose is preferably presented as two, three, four, five, six or more sub-doses administered at appropriate time intervals throughout the day. These sub-doses may be administered in unit dosage form, for example, containing from about 0.5 to 25 mg, preferably from about 2.5 to 10 mg, and most preferably from about 5 to 7 mg of active ingredient per unit dosage form.

For transplantation therapy, the desirable dose should be administered 4–12 days prior to transplantation and continued post-operatively 1–2 weeks and then tapered off 5% per week to a maintenance level of 5–10 mg/kg/day. Other therapies would be at 5–10 mg/kg/day. Ideally, the active ingredient should be administered to achieve peak plasma concentrations of the active ingredient of from about 1 to 100 μM, preferably from about 5 to 8 μM, most preferably about 7.5 to 50 μM. This may be achieved, for example, by the intravenous injection of a 0.1 to 5% solution of the active ingredient, optionally in saline, or orally administered as a bolus containing about 1 to about 100 mg/kg of the active ingredient. Desirable blood levels may be maintained by continuous infusion to provide about 0.01 to about 5.0 mg/kg/hour or by intermittent infusions containing about 0.4 to about 15 mg/kg of the active ingredient.

While it is possible for the active ingredient to be administered alone, it is preferable to present it as a pharmaceutical formulation. The formulations of the present invention comprise the active ingredient, as defined above, together with at least one pharmaceutically acceptable carrier, diluent or excipient. Preferred formulations include those adapted for oral, rectal, nasal, topical (including buccal and sublingual), vaginal or parenteral (including subcutaneous, intramuscular, intravenous and intradermal) administration. The formulations may conveniently be presented in unit dosage form and may be prepared by methods well known in the art of pharmacy. Such methods include the step of bringing into association the active ingredient with the carrier which constitutes one or more accessory ingredients. In general, the formulations are prepared by uniformly and intimately bringing into association the active ingredient with liquid carriers or finely divided solid carriers or both, and then, if necessary, shaping the product.

Formulations of the present invention adapted for oral administration may be presented as discrete units such as capsules or tablets each containing a predetermined amount of the active ingredient; as a powder or granules; as a solution or a suspension in an aqueous or non-aqueous liquid; or as an oil-in-water liquid emulsion or a water-in-oil liquid emulsion. The active ingredient may also be presented as a bolus, electuary or paste.

A tablet may be made by compression or molding, optionally with one or more accessory ingredients. Compressed tablets may be prepared by compressing in a suitable machine the active ingredient in a free-flowing form such as a powder or granules, optionally mixed with a binder (e.g., povidone, gelatin, hydroxypropylmethyl cellulose), lubricant, inert diluent, preservative, disintegrant (e.g., sodium starch glycolate, cross-linked providone, cross-linked sodium carboxymethyl cellulose) surface-active or dispersing agent.

Molded tablets may be made by molding in a suitable machine a mixture of the powdered compound moistened with an inert liquid diluent. The tablets may optionally be coated or scored and may be formulated so as to provide slow or controlled release of the active ingredient therein using, for example, hydroxypropyl-methyl cellulose in varying proportions to provide the desired release profile. Tablets may optionally be provided with an enteric coating, to provide release in parts of the gut other than the stomach.

Formulation adapted for topical administration in the mouth include lozenges comprising the active ingredient in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

Formulations adapted for rectal administration may be presented as a suppository with a suitable base comprising for example cocoa butter or salicylate.

Formulations adapted for vaginal administration may by presented as pessaries, tampons, creams, gels, pasted, foams or spray formulations containing in addition to the active ingredient such carriers as are known in the art to be appropriate.

Formulations adapted for parenteral administration include aqueous and non-aqueous isotonic sterile injection solutions which may contain antioxidants, buffers, bacteriostats and solutes which render the formulation isotonic with the blood of the intended recipient; and aqueous and non-aqueous sterile suspensions which may include suspending agents and thickening agents. The formulations may be present in unit-dose or multi-dose sealed containers, for example, ampules and vials, and any be stored in a freeze-dried (lyophilized) condition requiring only the addition of the sterile liquid carrier, for example water for injections, immediately, prior to use. Extemporaneous injection solutions and suspensions any be prepared from sterile powders, granules and tablets of the kind previously described.

Preferred unit dosage formulations as those containing a daily dose or unit, daily sub-dose, as herein above recited, or an appropriate fraction thereof, of an active ingredient.

It should be understood that in addition to the ingredients particularly mentioned above the formulations of this invention may include other agents conventional in the art having regard to the type of formulation in question, for example, those suitable for oral administration may include such further agents as sweeteners, thickeners and flavoring agent.

The present invention will be further illustrated with reference to the following examples which aid in the understanding of the present invention, but which are not to be construed as limitations thereof. all percentages report herein, unless otherwise specified, are percent by weight. All temperatures are expressed in degrees Celsius.

EXAMPLE 1

Preparation by Fermentation of Sesbanimide

A. Inoculum Preparation

Prepare a seed culture inoculating test tubes with 5 ml of a medium having the following composition.

| | |
|---|---|
| Tryptone | 5 g |
| Yeast extract | 2 g |
| Glucose | 1 g |
| Maltose | 1 g |
| $Na_2SO_4$ | 10 g |
| NaCl | 25.6 g |
| $Na_2SO_4$ | 4 g |
| $MgCl_2$ | 1.1 g |
| $CaCl_2$ | 1.13 g |
| KCl | 0.723 g |
| $NaHCO_3$ | 0.202 g |
| NaBr | 0.083 g |
| Tap water | 1000 ml |

Adjust pH to 7.0, sterilize the broth and after cooling add a frozen culture of Agrobacterium sp PH-103. Cultivate the bacterium at 28° C. for 30 hours with orbital agitation at 250 rpm. Inoculate aseptically with 7.5 ml of the above culture a shaking flask of 1000 ml capacity with 150 ml of sterile culture medium as defined below.

| | |
|---|---|
| Tryptone | 20 g |
| Yeast extract | 5 g |
| Dextrose | 20 g |
| MOPS | 2 g |
| $Na_2SO_4$ | 10 g |
| NaCl | 25.6 g |
| $Na_2SO_4$ | 4 g |
| $MgCl_2$ | 1.1 g |
| $CaCl_2$ | 1.13 g |
| KCl | 0.723 g |
| $NaHCO_3$ | 0.202 g |
| NaBr | 0.083 g |
| Tap water | 1000 ml |

Adjust pH to 7.0 with an alkali solution. Cultivate at 28° C. for 28 hours with orbital agitation at 250 rpm. Inoculate under sterile conditions with 25 ml of this culture a 2000 ml capacity flask containing 500 ml of the same culture medium. Incubate the flasks at 28° C. for 28 hours with orbital agitation at 200 rpm.

B. Fermentation

Sterilize at 122° C. for 30 minutes a fermentor of 75 liters capacity with 50 liters of the production medium described below. Adjust previously pH to 7.3 with a sterile alkali solution:

| | |
|---|---|
| Tryptone | 20 g |
| Yeast extract | 5 g |
| Dextrose | 5 g |
| Maltose | 4 g |
| $CaCO_3$ | 4 g |
| $Na_2SO_4$ | 10 g |
| NaCl | 25.6 g |
| $Na_2SO_4$ | 4 g |
| $MgCl_2$ | 1.1 g |
| $CaCl_2$ | 1.13 g |
| KCl | 0.723 g |
| $NaHCO_3$ | 0.202 g |
| NaBr | 0.083 g |
| Antifoaming agent (Emusil 7460) | 0.8 ml |
| Tap water | 1000 ml |

Inoculate the fermentor with 2000 ml of the third stage inoculum. Incubate the fermentation culture at 28° C. with an agitation of 250 rpm and aeration at a rate of 25 liters/minute. An overpressure of 0.5 bars is needed during the process.

C. Isolation

After completion of the cultivation, adjust pH of the broth to 7.0 with acetic acid and remove the solids by a continuous centrifugal separator. Extract the supernatant portion (48 liters) twice with 25 liters of ethyl acetate. Desiccate the combined organic phases with sodium sulfate, filter and concentrate to dryness under vacuum to yield 11–10 g of a crude residue containing the sesbanimide.

EXAMPLE 2

Separation of Sesbanimide From Crude Extracts

Dissolve the crude residue in 800 ml of water:methanol (1:1) which was defatted by partitioning twice with 500 ml of hexane. Extract the water/alcohol fraction twice with 400 ml of methylene chloride and twice with 400 ml of ethyl acetate. Concentrate the organic solvent solubles in an evaporator yielding 2 g of active organic extracts. Chromatograph 1.9 g of organic extract in silica gel by an MPLC system using a mixture of hexane/ethyl acetate as the eluting solvent. The immunosuppressive and antitumoral activities are detected in fractions 5–7 (300 mg), eluted with hexane/ethyl acetate 4:6–3:7. Further concentration may be achieved by MPLC in silica gel using a step-wise gradient of ethyl acetate in hexane. 50 ml each of hex/AcOEt (4:6) (3:7) (2:8) (1:9) and ethyl acetate. Combine similar fractions in the basis of TLC analysis, and the most active fractions 6–8, 35 mg are eluted with hexane/ethyl acetate 25:75. Continue separation with active fractions 6–8 by column chromatography in C18 reversed phase using $H_2O$:methanol (87:13) as the eluting solvent. Activity is located in fractions 3–4, to yield 12 mg of a pure compound.

EXAMPLE 3

Biological Assay Descriptions

Mixed Lymphocyte Reaction (MLR)

The MLR is an in vitro test of cellular immunity in which murine lymphocytes from genetically dissimilar animals are cocultured to mutually induce cell proliferation (i.e., two-way MLR method). Mixed cell suspensions, together with the test compound, are incubated for 96 hours and subsequently pulsed for 15 hours with tritiated-thymidine (3H-Thy), a radioisotopically labelled nucleic acid. Tritiated-thymidine is incorporated into the DNA of proliferating cells. Data from the MLR is generated as dpm of radioactivity which is then expressed as a percentage of cellular activity, relative to control, using the following reduced formula:

$$\left| \frac{\text{Experimental value} - (Balb/c - C57Bl/6 - \text{Media})}{\text{Positive Control} - (Balb/c - C57Bl/6 - \text{Media})} \right| * 100$$

A 50% inhibitory concentration (IC$_{50}$) value was interpolated for sesbanimide containing fractions tested. A ratio between cytotoxicity, as determined from the LcV described below, and activity in the MLR is also presented. A high ratio distinguishes noncytotoxic immunosuppression from general cytotoxicity.

Procedure

Reconstituted extract (10 µl) is added in two sets of duplicates into wells of a 96-well microtiter plate and evaporated to dryness at room temperature. Mixed lymphocytes from Balb/c (H-2$^d$) and C57Bl/6 (H-2$^b$) mice are cocultured at 2.5×10$^6$ cells/ml in the presence of sample, alone or separately with cyclosporin A standard. To the other set of sample duplicates is added complete media without cells so as to provide for background color control data. All plated are incubated in a 5% CO$_2$ incubator for 96 hours and pulsed for 15 hours with 100 µl containing 1 µCi/well tritiated-thymidine ($^3$H-Thy). The plates are harvested onto glass fiber filter discs using an INOTECH harvester. The filter discs are counted directly using an INOTECH dry scintillation counter. The activity of the discs are calculated as a relative proliferative percent of a mean control value as described above.

Lymphocyte Cytotoxicity (LcV) Assay

The LCV is a in vitro cytotoxicity assay for murine lymphocytes designed by the investigator. The LCV is similar to the MLR with the exception that only one cell population (Balb/c) is incubated with the test compound to assess cytotoxicity as distinct from the antiproliferative effects of a test compound. That is, unlike the unambiguous determination of immunostimulation from MLR data, a judgement of immunosuppression can not be immediately interpreted. Cytotoxicity (e.g., due to direct cell lysis) from a compound can occur which would alter viability determinations inherent in the generation of MLR data. To ensure that cytotoxicity to the lymphocytes does not account for low data values, a parallel assay is performed. The percent viable cells is determined by the MTT-thiazolyl blue method after a similar incubation to the MLR of lymphocytes with the test sample. MTT is a substrate converted by mitochondrial enzymes in living cells to a purple, water-insoluble, formazan crystal. If there is no significant reduction in cell viability, as determined by this detection method, then damaged cells are probably not present for low data values generated in the MLR. Colorimetric data from the LCV is calculated as a percentage of viability, relative to control, using the following formula:

$$\left| \frac{\text{Experimental value} - (\text{Nonspecific Color})}{\text{Positive Control} - (\text{Media})} \right| * 100$$

A 50% viability, or 50% cytotoxicity, (IC$_{50}$) value was interpolated for sesbanimide containing fractions tested.

Procedure

Lymphocytes are prepared as described above for the MLR with the exception that cells from only one murine strain are prepared (BLAB/c). Reconstituted extract (10 µl) is added in two sets of duplicates into wells of a 96-well microtiter plate and evaporated to dryness at room temperature. Lymphocytes (2.5×10$^6$ cells/ml) are added to one set of duplicates and to wells containing no sample. Media containing no cells are added to the other set of duplicates to provide background color control data. Plated are incubated in a 5% CO$_2$ incubator for 4 hours and pulsed with MTT-thiazolyl blue for 6–8 hours.

In Vivo Efficacy Models

In vivo models are used to evaluate the efficacy and toxicity of immunomodulatory agents. Demonstration of in vivo efficacy is a critically important criterion for developing these agents to clinical trial and no acceptable alternative is available for predicting activity or toxicity in living systems. Agents to be studied are expected to be novel in structure and possibly mechanism of action. More than 1000 mice are used per year in the course of these studies. Animals are C57Bl/6, Balb/c, CD-1 and CB6-F 1 strains and are 3–7 weeks of age.

Mice are transported to the facility in an environmentally controlled vehicle, are quarantined for 1–2 weeks, are housed 5 per cage, fed food and water and be inspected for signs of disease or ill-health prior to release from quarantine. A consultant veterinarian specialist in laboratory animal care will be used on a routine and repeated basis to insure the humane treatment of animals and the safety of personnel. The research facility will be designed to deliver 10–15 changes of nonrecirculated air per hour at a temperature of 75 degrees (+/−2 degrees) and a relative humidity of 50% (+/−10%). Anesthetics are used if necessary to avoid unnecessary discomfort or pain to animals resulting from experimental procedures. Research will be guided at all times by "Principles for the Utilization and Care of Vertebrate Animals Used in Testing, Research and Training" and the "Guide for the Care and Use of Laboratory Animals".

Toxicology

The MTD establishes the parameters to establish in vivo dosages initiated for studying the Graft-v-Host reaction and skin grafting. The Swiss conventional mouse (Charles River CD-1) is used in a weight range from 18–30 g.

Procedure

Animals are injected with a single dose at four dose levels: e.g., 400 mg/kg, 100 mg/kg, 40 mg/kg, and 10 mg/kg in 0.5 ml of sterile vehicle (2 animals per dose, MTD). A saline solution containing 5% non-denatured EtOH and a drop of Tween-80 detergent is used a vehicle for dilution. Stirring and sonication are utilized to effect solution or suspension of the composition. The composition is injected within one hour of preparation. Animals are observed for five days (MTD) after injection for toxic symptoms and/or death. Group weights are taken D0 and D5. Surviving animals are sacrificed on D5 (MTD). A 'Daily Logsheet' used in the toxicity studies is appended. Drug Doses are listed below:

Graft-vs-Host Reaction (GVHR)

The GVHR used for in vivo screening is a modification of the Simonsen's technique. The F$_1$ hybrid host animal is grafted with immunocompetent spleens cells from a parent strain. The host spleen cells are incompatible to grafted donor cells but are themselves not competent to react against them (shared parental genetic determinants). The rejection mechanism in this model is, therefore, from the graft toward the host. The grafted cells, via intraperitoneal injection, migrate to the host's spleen. There they proliferate in response to the difference in genetic determinants inherited from the other parental strain. The index used to measure the success of the GVHR is spleenomegally (increased spleen weight due to cellular proliferation of grafted lymphocytes). An index of 1.0 is equivalent to the spleen weight of syngeneic grafted controls. An index>1.3 (graft index) is considered to be a successful graft rejection of the recipient animal. Any sample that prevents splenomegaly (<graft index) is considered as an immunosuppressive active. Likewise, enhancement of splenomegaly (>graft index) is due either to immunostimulatory synergy of the response or nonspecific immunostimulation. This assay is a cell-mediated type of response and is the direct in vivo correlate of the MLR.

The GVHR is widely used as an in vivo model in transplantation research laboratories. As in models for delayed sensitivity and allograft rejection, it also has clinical implications, especially in bone marrow transplantation. In this situation, immunocompetent lymphocytes transferred with the transplanted bone marrow cells can recirculate into the host bone marrow. These cells from the graft can react against the host (i.e., graft-vs-host disease) with deleterious consequences. An immunosuppressant discovered by this in vivo model would be useful in preventing or alleviating the complications due to severe graft- vs-host disease.

Procedure

The highest test dose is selected from a previously determined maximum tolerated dose (MTD) resulting from a once only intraperitoneal (i.p.) injection of two animals/dose (e.g., 400, 100, 40 and 10 mg/kg) These animals are followed for five days to allow for possible toxic side effects of the test compound.

In the GVHR, male, CB6-F 1 mice ($H2^d+H2^b$) are grafted by i.p. injection of 50×106 Balb/c ($H2^d$) splenic lymphocytes conditioned in high-glucose (4500 mg/L) Dulbecco's modified Eagles medium. After a minimum of 16 hours has elapsed to allow for grafted cell absorption and migration into the host spleen, groups of animals (6/group) then receive the highest tolerated dose of test compound (previously determined) or one of three lower doses (log drops) by i.p. injection per diem, for 7 days. Grafted positive controls, nongrafted negative controls and syngeneic grafted animals all receive vehicle i.p. injections during this time. A standard of cyclophosphamide (200 mg/kg) is used. Experimental animals are sacrificed on D8 and spleens removed. The data is reported as a spleen index compared to the weight of the syngeneic control spleen—both corrected for the total body weights of the animals. In addition, the spleens are homogenized and the lymphocytes enumerated and viabilities determined. The data from both determinations are also expressed as a percent immunomodulation of the positive controls. all data is corrected for nonspecific effects measured from nongrafted animals. Moribund animals are sacrificed immediately.

Skin Grafting

Skin grafting is used to assess altered T cell function by immunosuppressive active compounds identified in the GVHR. The general usefulness of this model is appreciated as a direct correlate to human transplantation procedures. In this way, a putative immunosuppressive compound is screened for its ability to prevent or alleviate severe host-vs-graft disease due to allograft rejection. Currently, the procedure utilizes the same genetic strains of mice as in the GVHR; namely, the Balb/c and CB6-F 1 strains.

Procedure

Skin grafts are prepared by dermal punches (1–2 cm., diameter) from the skin of a sacrificed male CB6-F 1 mice ($H2^d+H2^b$). These are placed into a solution of normal saline until further use. The grafts are applied at 180 ° to their original orientation to the dermal punched backs of anesthetized (90 mg/kg ketamine.HCl and 10 mg/kg rompun) recipient male Balb/c ($H2^d$) mice. A liquid bandage is applied to the grafted area of the recipient animals by using an aerosol form of a Collodion (containing no clove extracts of other fragrances)/isopropanol solution. On D1 (>16 hours), groups of individually caged animals (5/group) receive an i.p. injection per diem of an active dose of test compound, as previously determined in the GVHR, for as long as the graft survives up to 30 days. Grafts that slough-off on or before D3 post transplantation are considered 'no takes'. Normal graft rejection in control animals occurs between day 5–6 post transplantation. Beyond D6, evaluation of the grafted skin is graded daily for the following characteristics: erythema, crusting, purulent discharges, sensation of the grafted skin and status of the hair (occurring in prolonged graft survival studies). 'No takes', control animals post D6 and moribund animals are sacrificed. Experimental animals are sacrificed on the day of graft rejection or D30, whichever come first.

The present invention has been described in detail, including the preferred embodiments thereof. However, it will be appreciated that those skilled in the art, upon consideration of the present disclosure, may make modifications and/or improvements on this invention and still be within the scope and spirit of this invention as set forth in the following claims.

What is claimed is:

1. A fermentation process for producing and accumulating the compound sesbanimide, which has the following structure:

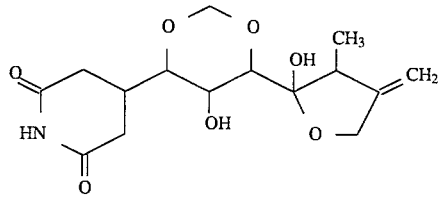

comprising cultivating Agrobacterium PH-103, CECT 4458 under controlled aerobic fermentation conditions in an aqueous nutrient medium at about neutral pH, and at from about 25° to about 30° C. for from about 30 to about 100 hours, followed by recovery of sesbanimide from the medium.

2. The process of claim 1, wherein the compound sesbanimide is isolated from the cultured broth by:
   a. separating the solids from the broth;
   b. extracting the filtrate broth with an immiscible extraction solvent;
   c. concentrating the extraction solvent to dryness;
   d. diluting the residue with saturated aqueous NaCl and 10% methanol 1:1 and portion with an immiscible solvent;
   e. removing the active materials from the aqueous alcohol fraction by partitioning with an appropriate solvent;
   f. combining and concentrating the recovered solvent phases containing the crude active material; and
   g. purifying the sesbanimide from the crude concentrated material by use of one or more chromatographic techniques.

* * * * *